US006461646B2

(12) United States Patent
Ito

(10) Patent No.: US 6,461,646 B2
(45) Date of Patent: Oct. 8, 2002

(54) PHARMACEUTICAL COMPOSITION FOR PREVENTING AND/OR CURING DIGESTIVE DISORDERS

(75) Inventor: Mikio Ito, Aichi (JP)

(73) Assignees: Lintec Corporation, Tokyo (JP); Sinanen Zeomic Co., Ltd., Nagayo (JP)

( * ) Notice: Subject to any disclaimer, the term of this patent is extended or adjusted under 35 U.S.C. 154(b) by 0 days.

(21) Appl. No.: 09/916,582

(22) Filed: Jul. 30, 2001

(65) Prior Publication Data

US 2002/0001628 A1 Jan. 3, 2002

Related U.S. Application Data

(62) Division of application No. 09/694,255, filed on Oct. 24, 2000.

(30) Foreign Application Priority Data

Nov. 24, 1999 (JP) ............................................. 11-332691

(51) Int. Cl.$^7$ ........................ H01K 59/16; A61K 33/22; A61K 31/54; A01N 25/00
(52) U.S. Cl. ........................ 424/618; 424/154; 424/405; 424/660; 514/222.5
(58) Field of Search .................................. 424/154, 402, 424/618, 660; 514/222.5

(56) References Cited

U.S. PATENT DOCUMENTS

| 4,537,771 A | 8/1985 | Greb et al. |
| 4,938,958 A | 7/1990 | Niira et al. |
| 5,326,567 A | 7/1994 | Capelli |
| 5,744,151 A | 4/1998 | Capelli |

FOREIGN PATENT DOCUMENTS

| JP | 1-257124 | 10/1989 |
| JP | 4-244029 | 9/1992 |

*Primary Examiner*—Jose' G. Dees
*Assistant Examiner*—R Dewitty
(74) *Attorney, Agent, or Firm*—Armstrong, Westerman & Hattori, LLP

(57) ABSTRACT

The invention provides a pharmaceutical composition for preventing and/or curing digestive disorders such as digestive ulcers, gastritis, etc. The pharmaceutical composition contains, as the active ingredient, an aluminosilicate having silver and zinc ions, and it has an excellent effect for protecting gastric mucous membrane and an excellent effect of promoting the curing of a gastric ulcer.

22 Claims, No Drawings

PHARMACEUTICAL COMPOSITION FOR PREVENTING AND/OR CURING DIGESTIVE DISORDERS

This application is a division of application Ser. No. 09/694,255, filed Oct. 24, 2000.

BACKGROUND OF THE INVENTION

1. Field of the Invention

The present invention relates to a pharmaceutical composition for preventing and/or curing digestive disorders such as digestive ulcers, gastritis, etc.

2. Description of the Related Art

It is said that digestive disorders such as typically gastric ulcers are so-called national diseases much seen in Japan, and the rate of the diseases in Japan is higher than that in other countries. Accordingly, various medicines for such digestive disorders have heretofore been developed and put into practical use. At present, however, better medicines for digestive disorders are desired.

SUMMARY OF THE INVENTION

The object of the present invention is to provide a pharmaceutical composition for preventing and/or curing digestive disorders such as digestive ulcers, gastritis, etc.

In the situation as above, we, the present inventors have assiduously studied and have found that aluminosilicates having silver and zinc ions are effective for preventing and/or curing digestive disorders.

In Japanese Patent Laid-Open No.244029/1992, described is an antimicrobial endermic preparation for external application which comprises, as the active ingredient, an aluminosilicate having silver and zinc ions. However, this has no relation to the potency of preventing and/or curing digestive disorders.

Based on our finding as above, we, the inventors have completed the present invention. Specifically, the invention provides a pharmaceutical composition for preventing and/ or curing digestive disorders, which is characterized in that it contains, as the active ingredient, an aluminosilicate having silver and zinc ions.

Preferably, the aluminosilicate in the pharmaceutical composition is zeolite.

Also preferably, the pharmaceutical composition is for preventing and/or curing digestive ulcers or gastritis.

According to the invention, there is provided such a pharmaceutical composition for preventing and/or curing digestive disorders such as digestive ulcers, gastritis, etc. The pharmaceutical composition contains, as the active ingredient, an aluminosilicate having silver and zinc ions, and it has an excellent effect for protecting gastric mucous membrane and an excellent effect of promoting the curing of a gastric ulcer.

DETAILED DESCRIPTION OF THE INVENTION

The pharmaceutical composition of the invention for preventing and/or curing digestive disorders contains, as the active ingredient, an aluminosilicate having silver and zinc ions.

The digestive disorders to which the invention is directed include, for example, digestive ulcers such as an esophageal ulcer, a gastric ulcer and a duodenal ulcer, and also esophagitis, gastritis, enteritis and enterogastric intestinal hemorrhage. Of those, the pharmaceutical composition of the invention is especially effective for curing a gastric ulcer, a duodenal ulcer and gastritis.

The aluminosilicate for use in the invention may be any of a crystalline aluminosilicate generally referred to as zeolite, or an amorphous aluminosilicate.

Zeolite for use herein may be any of natural zeolite or synthetic zeolite, including, for example, A-type zeolite, X-type zeolite, Y-type zeolite, T-type zeolite, sodalite, mordenite, analcime, clinobutyrolite, chabazite, erionite, etc.

Preferably, the aluminosilicate has an average particle diameter falling between 0.5 $\mu$m and 20 $\mu$m for its better dispersibility.

Regarding the amount of the silver and zinc ions in the aluminosilicate, it is desirable that the silver ions account for from 0.3% to 40% and the zinc ions for from 1% to 15% for ensuring long-lasting potency and stability of the pharmaceutical composition. The percentage, %, referred to herein is meant to indicate weight percentage of silver and zinc in the aluminosilicate dried at 110° C.

The aluminosilicate having silver and zinc ions for use in the invention can be formulated, for example, according to the method described in the above-mentioned Japanese Patent Laid-Open No. 244029/1992.

Along with additives thereto, such as vehicle, binder, disintegrator, solubilizer, etc., the aluminosilicate having silver and zinc ions can be formulated in any known manner into oral preparations such as tablets, capsules, powders, granules, liquids for internal application, etc.

The oral dose of the aluminosilicate having silver and zinc ions may be appropriately determined, depending on the condition of the patient who takes it. In general, it may fall between 100 mg/day/adult and 10000 mg/day/adult.

EXAMPLES

An aluminosilicate having silver and zinc ions, Zeomic AJ10N (trade name, a commercial product of Sinanen Zeomic Co., LTD.—this has an average particle diameter of 2.5 $\mu$m, and contains 2.2% of silver ions and 12.5% of zinc ions—hereinafter referred to as Ag,Zn—ABZ) was tested as in the following Test Examples.

Test Example 1

Effect for Protecting Gastric Mucous Membrane

Test Method:

After 24-hours abstinence from feed, male SD rats (body weight: about 200 g) were orally dosed with a suspension of Ag,Zn—ABZ (dose: 75 mg/10 ml/kg (body weight), 150 mg/10 ml/kg (body weight), or 300 mg/10 ml/kg (body weight)). After one hour, they were orally dosed with absolute ethanol (10 ml/kg (body weight)). After further one hour, the stomach was taken out of each rat, and this was cut open along its greater curvature. The inflamed area of the gastric mucous membrane was measured, and the data were compared with each other to determine the degree of the gastric mucous membrane damage of each rat.

As the vehicle in place of the suspension of Ag,Zn—ABZ, pure water (10 ml/kg (body weight)) was dosed to control rats, and the thus-dosed control rats were evaluated in the same manner as herein.

Test Result:

The test result is shown in Table 1 below. As is obvious from Table 1, Ag,Zn—ABZ strongly protected the gastric mucous membrane of the rats. Even at the dose of 75 mg/kg (body weight), the compound significantly inhibited the damage of the gastric mucous membrane of the rats. The test result supports the excellent potency of the compound to protect the gastric mucous membrane.

The gastric mucous membrane of the rats dosed with the compound, Ag, Zn—ABZ was macroscopically observed, and was found to have a white mask of the compound on its surface. This indicates the strong adhesiveness of the compound to the gastric mucous membrane. It is believed that the characteristic of the compound will augment the excellent potency of the compound to protect the gastric mucous membrane.

TABLE 1

| Test Compound | Dose (mg/kg) | Inflamed Area (mm$^2$)$^a$ |
|---|---|---|
| Ag, Zn-ABZ | 75 | 10.9 ± 3.3** |
| Ag, Zn-ABZ | 150 | 3.6 ± 1.7** |
| Ag, Zn-ABZ | 300 | 1.3 ± 0.7** |
| Vehicle | — | 148.6 ± 11.2 |

N = 8
$^a$average value ± standard deviation
**P < 0.01 vs Vehicle (Dunnett's multiple comparison)

Test Example 2

Effect of Promoting the Curing of Gastric Ulcer

Test Method:

From 3 days before ulcer induction to the end of the test period, male SD rats (body weight: about 200 g) were bred in such a controlled manner that their daily feed intake time was limited to only 2 hours, between 10:00 and 11:00 AM and between 6:00 and 7:00 PM. With their daily feed intake time being thus limited, the rats were subjected to ulcer induction with 0.02 ml of 20% acetic acid injected into the wall of the stomach via the serous tunic thereof. Everyday from the next day after the acetic acid injection up to day 14, a suspension of Ag,Zn—ABZ was orally dosed to the rats (75 mg/10 ml/day/kg (body weight), 150 mg/10 ml/day/kg (body weight), or 300 mg/10 ml/day/kg (body weight)) twice a day (at 9:30 AM and at 5:30 PM). On day 15, the stomach was taken out of each rat, and this was cut open along its greater curvature. The area of the ulcer site was measured, and the data were compared with each other to evaluate the effect of the compound, Ag,Zn—ABZ to promote the curing of the gastric ulcer of the rats.

As the vehicle in place of the suspension of Ag,Zn—ABZ, pure water (10 ml/day/kg (body weight)) was dosed to control rats, and the thus-dosed control rats were evaluated in the same manner as herein.

Test Result:

The test result is shown in Table 2 below. As is obvious from Table 2, Ag,Zn—ABZ had an excellent effect of promoting the curing of the gastric ulcer.

TABLE 2

| Test Compound | Dose (mg/kg) | Ulcer Area (mm$^2$)$^a$ |
|---|---|---|
| Ag, Zn-ABZ | 75 | 5.8 ± 1.2 |
| Ag, Zn-ABZ | 150 | 3.5 ± 0.5** |
| Ag, Zn-ABZ | 300 | 0.4 ± 0.4** |
| Vehicle | — | 8.1 ± 0.9 |

N = 7
$^a$average value ± standard deviation
**P < 0.01 vs Vehicle (Dunnett's multiple comparison)

Formulation Example

Tablet

| | |
|---|---|
| Ag, Zn-ABZ | 250 mg |
| Carboxymethyl Cellulose | 100 mg |
| Starch | 20 mg |
| Crystalline Cellulose | 160 mg |
| Magnesium Stearate | 8 mg |
| Total | 538 mg |

Safety Test:

In the acute toxicity test (oral administration to rats) of the compound, Ag,Zn—ABZ, $LD_{50}$ of the compound was more than 5000 mg/kg (body weight).

The experiments on male SD rats showed that the aluminosilicate having silver and zinc ions has an excellent effect for protecting gastric mucous membrane and an excellent effect of promoting the curing of a gastric ulcer. The test results suggest the efficacy of the aluminosilicate having silver and zinc ions even in an acidic condition of around pH 2.0. Accordingly, the aluminosilicate having silver and zinc ions is effective for preventing and/or curing digestive disorders.

While the invention has been described in detail and with reference to specific embodiments thereof, it will be apparent to one skilled in the art that various changes and modifications can be made therein without departing from the spirit and scope thereof.

What is claimed is:

1. A method of treating digestive disorders selected from the group consisting of an esophageal ulcer, a duodenal ulcer, esophagitis gastritis, enteritis and enterogastric intestinal hemorrage, comprising the step of administering orally to a mammal in need thereof a composition comprising an effective amount of an aluminosilicate having silver and zinc ions.

2. The method as claimed in claim 1, wherein the aluminosilicate is zeolite.

3. The method as claimed in claim 1, wherein said digestive disorders are selected from the group consisting of an esophageal ulcer, a gastric ulcer, a duodenal ulcer and gastritis.

4. The method as claimed in claim 2, wherein said digestive disorders are digestive ulcers or gastritis.

5. The method as claimed in claim 1, wherein said mammal is a human subject.

6. The method as claimed in claim 2, wherein said mammal is a human subject.

7. The method as claimed in claim 1, wherein the aluminosilicate has an average particle size between 0.5 µm and 20 µm.

8. The method as claimed in claim 2, wherein the zeolite has an average particle size between 0.5 µm and 20 µm.

9. The method as claimed in claim 1, wherein the silver ion content in the aluminosilicate is from 0.3% to 40% and the zinc ion content is from 1% to 15% as measured by the weight percentage of silver and zinc, respectively, in the aluminosilicate dried at 110°C.

10. The method as claimed in claim 2, wherein the silver ion content in the zeolite is from 0.3% to 40% and the zinc ion content is from 1% to 15% as measured by the weight percentage of silver and zinc, respectively, in the aluminosilicate dried at 110°C.

11. The method as claimed in claim 1, wherein the aluminosilicate having silver and zinc ions is administered at a dosage between 100 mg/day/adult and 10,000 mg/day/adult.

12. The method as claimed in claim 2, wherein the zeolite having silver and zinc ions is administered at a dosage between 100 mg/day/adult and 10,000 mg/day/adult.

13. A method of protecting the gastric mucous membrane of a mammal, comprising the step of administering orally to a mammal in need thereof a composition comprising an effective amount of an aluminosilicate having silver and zinc ions.

14. The method as claimed in claim 13, wherein the aluminosilicate is zeolite.

15. The method as claimed in claim 13, wherein said mammal is a human subject.

16. The method as claimed in claim 14, wherein said mammal is a human subject.

17. The method as claimed in claim 13, wherein the aluminosilicate has an average particle size between 0.5 µm and 20 µm.

18. The method as claimed in claim 14, wherein the zeolite has an average particle size between 0.5 µm and 20 µm.

19. The method as claimed in claim 13, wherein the silver ion content in the aluminosilicate is from 0.3% to 40% and the zinc ion content is from 1% to 15% as measured by the weight percentage of silver and zinc, respectively, in the aluminosilicate dried at 110°C.

20. The method as claimed in claim 14, wherein the silver ion content in the zeolite is from 0.3% to 40% and the zinc ion content is from 1% to 15% as measured by the weight percentage of silver and zinc, respectively, in the aluminosilicate dried at 110°C.

21. The method as claimed in claim 13, wherein the aluminosilicate having silver and zinc ions is administered at a dosage between 100 mg/day/adult and 10,000 mg/day/adult.

22. The method as claimed in claim 14, wherein the zeolite having silver and zinc ions is administered at a dosage between 100 mg/day/adult and 10,000 mg/day/adult.

* * * * *

UNITED STATES PATENT AND TRADEMARK OFFICE
CERTIFICATE OF CORRECTION

PATENT NO.   : 6,461,646 B2
DATED        : October 8, 2002
INVENTOR(S)  : Mikio Ito It is certified that error appears in the above-identified patent and that said Letters Patent is hereby corrected as shown below:

<u>Column 4,</u>
Line 32, after "esophageal ulcer," insert -- a gastric ulcer, --
Line 33, insert -- , -- after "esophagitis"

Signed and Sealed this

Twenty-ninth Day of April, 2003

JAMES E. ROGAN
*Director of the United States Patent and Trademark Office*